United States Patent
Hazenkamp et al.

(10) Patent No.: US 10,064,409 B2
(45) Date of Patent: Sep. 4, 2018

(54) SYNERGISTIC ANTIMICROBIAL FORMULATION

(71) Applicant: BASF SE, Ludwigshafen (DE)

(72) Inventors: Menno Hazenkamp, Riehen (CH); Gabriele Bönemann, Lörrach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/888,422

(22) PCT Filed: Apr. 29, 2014

(86) PCT No.: PCT/EP2014/058657
§ 371 (c)(1),
(2) Date: Oct. 30, 2015

(87) PCT Pub. No.: WO2014/177530
PCT Pub. Date: Nov. 6, 2014

(65) Prior Publication Data
US 2016/0058005 A1  Mar. 3, 2016

(30) Foreign Application Priority Data

May 3, 2013 (EP) .................................. 13166413
Oct. 1, 2013 (EP) .................................. 13186800
Oct. 9, 2013 (EP) .................................. 13187830

(51) Int. Cl.
*A01N 41/04* (2006.01)
*A01N 31/16* (2006.01)
*A01N 37/02* (2006.01)
*C11D 3/24* (2006.01)
*C11D 3/48* (2006.01)
*C11D 3/34* (2006.01)

(52) U.S. Cl.
CPC ............. *A01N 41/04* (2013.01); *A01N 31/16* (2013.01); *A01N 37/02* (2013.01); *C11D 3/24* (2013.01); *C11D 3/3409* (2013.01); *C11D 3/48* (2013.01)

(58) Field of Classification Search
CPC ........ A01N 41/04; A01N 31/16; A01N 37/02; C11D 3/24; C11D 3/3409; C11D 3/48
See application file for complete search history.

(56) References Cited

U.S. PATENT DOCUMENTS

| | | | |
|---|---|---|---|
| 6,689,223 B1 * | 2/2004 | Meine | C11D 1/8305 134/2 |
| 2003/0185902 A1 | 10/2003 | Hei et al. | |
| 2014/0296349 A1 | 10/2014 | Both et al. | |

FOREIGN PATENT DOCUMENTS

| | | |
|---|---|---|
| CA | 1244759 A | 11/1988 |
| CA | 2267331 A1 | 4/1998 |
| DE | 3229097 A1 | 2/1984 |
| DE | 19640201 A1 | 4/1998 |
| EP | 0 709 507 A1 | 5/1996 |
| EP | 2 436 754 A1 | 4/2012 |
| JP | H0987109 A | 3/1997 |
| JP | 2002053899 A | 2/2002 |
| WO | WO-2007/139844 A2 | 12/2007 |

OTHER PUBLICATIONS

International Search Report in International Patent Application No. PCT/EP2014/058657, dated Jul. 29, 2014.
European Search Report in European Patent Application No. EP 13166413, dated Sep. 30, 2013.

* cited by examiner

*Primary Examiner* — Sahar Javanmard
(74) *Attorney, Agent, or Firm* — Marshall, Gerstein & Borun LLP; Steven M. Parks

(57) ABSTRACT

Home care formulation comprising a formulation of a sulfonic acid derivative and a carboxylic acid.

16 Claims, No Drawings

SYNERGISTIC ANTIMICROBIAL FORMULATION

CROSS-REFERENCE TO RELATED APPLICATIONS

This application is a National Stage Entry of International Application PCT/EP2014/058657 filed Apr. 29, 2014, which claims priority to EP 13166413.8, filed May 3, 2013, EP 13186800.2, filed Oct. 1, 2013, and EP 13187830.8, filed Oct. 9, 2013, wherein the contents of all foregoing applications are herein incorporated by reference in their entirety.

FIELD OF THE INVENTION

The present invention relates to a new formulation with antimicrobial activity, its use as a cleaning agent or disinfection agent or descaling agent as well as to a cleaning agent or disinfection agent or descaling agent comprising said formulation.

BACKGROUND OF THE INVENTION

Antimicrobial formulations are applied in various areas such as home care formulations, all-purpose-cleaners, bathroom cleaners, toilet-bowl cleaners, disinfectants, sanitary cleaners and clean-in-place (CIP) applications. CIP applications are used in practice in the food and beverage industry, like in breweries, in the dairy industry, in the soft-drink and juice manufacturing industry, but also in the cosmetic and pharmaceutical industry.

A huge number of biocides are known which have antimicrobial activity, among them aliphatic carboxylic acids need to be mentioned. Unfortunately important members of the class of aliphatic carboxylic acids with antimicrobial activity suffer from strong smell at least at effective concentrations. Further even though such aliphatic carboxylic acids show some biocidal effectivity their activity could be still enhanced.

Beside antimicrobial activity the descaling efficiency in most applications is of importance.

Thus the object of the present inventions is to provide a formulation with good antimicrobial activity and descaling efficiency without unpleasant odour.

SUMMARY OF THE INVENTION

It has now been found that the combination of a short chain carboxylic acid, i.e. a carboxylic acid with not more than 10 carbon atoms, and a non-aromatic sulfonic acid (such as typically methanesulfonic acid) shows both good antimicrobial properties and good properties in typical cleansing applications. The combination thus may be used with advantage as an antimicrobial agent, e.g. in typical cleansing formulations containing ingredients such as surfactants or further antimicrobial agents like chlorobenzene derivatives. The present invention thus provides a formulation comprising a short chain carboxylic acid, i.e. a carboxylic acid with not more than 10 carbon atoms, and a non-aromatic sulfonic acid compound.

Accordingly, one embodiment of the present invention is directed to a formulation comprising (a) a sulfonic acid (SA) of formula (I)

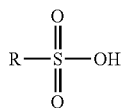

wherein
R is selected from the group consisting of linear alkyl residue, branched alkyl residue, linear alkenyl residue, and branched alkenyl residue; and
(b) at least one, preferably one, two or three, more preferably one, carboxylic acid (CA) selected from the group consisting of mono-carboxylic acid, di-carboxylic acid and tri-carboxylic acid.

The formulation of the present invention has good antimicrobial activity and descaling efficiency without pungent odour.

Accordingly in a further aspect of the invention the formulation as defined herein is used as an antimicrobial, especially as a bactericide and/or a fungicide.

In one embodiment the formulation of the present invention is used for antimicrobial treatment, antimicrobial accoutrement, desodoration, sanitization and/or disinfection of inanimate surfaces and materials.

In a further aspect the present invention is directed to a product comprising the formulation according to this invention, wherein said product is selected from the group consisting of home care formulation, disinfectant of hard and/or soft surfaces, sanitary detergent of hard and/or soft surfaces, and product for clean in place application.

The formulation according to this invention brings about the additional advantage of low corrosiveness to sensitive surfaces such as plastics surfaces (as, for example, commonly used in kitchen and bathroom installations and furniture, garden furniture etc.). The formulation according to this invention thus may be used with special advantage in cleaners and antimicrobial preparations commonly applied in these fields, such as all purpose cleaners, dishwashing liquids, bath room cleaners, kitchen cleaners, sanitary cleaners, furniture cleaners.

DETAILED DESCRIPTION OF THE INVENTION

In the following the invention is described in more detail.
The formulation of this invention must comprise the sulfonic acid (SA) and the carboxylic acid (CA) as defined in more detail below.

The term "formulation" is understood as known in this technical field, i.e. preferably as a preparation of compounds containing optionally adjuvants, wherein said formulation shows for a desired purpose measurable activity. In the present case the formulation shows in particular antimicrobal activity. Adjuvants are known to the skilled person and are selected depending on the specific use of the formulation. The selection of adjuvants is in the skilled knowledge and is not subject of this invention.

In one aspect of the invention the formulation is a dry formulation, e.g. a powder or a pressed formulation. In another aspect the formulation of this invention is in liquid form. In one specific aspect the formulation according to this invention is an aqueous formulation. Preferably the aqueous formulation contains at least 20 wt.-%, more preferably at least 30 wt.-%, still more preferably at least 40 wt.-%, $H_2O$.

Preferably the formulation, e.g. the aqueous formulation, has a pH in the range of 0 to 4.0, more preferably in the range of 0 to 3.0.

In one preferred embodiment the weight ratio between the sulfonic acid (SA) and the carboxylic acid (CA) [SA/CA] is in the range of 0.001 to 20.0, more preferably in the range of 0.01 to 20.0, still more preferably in the range of 0.01 to 15.0, like in the range of 0.1 to 8.0.

In one preferred embodiment, the formulation according to the invention can be a concentrate that has to be diluted with water prior to use. In another preferred embodiment the formulation can be a ready-to-use formulation that is used undiluted. Likewise products comprising the formulation can be concentrates or ready-to-use products.

If the formulation according to the invention is used undiluted ("ready-to-use"), the formulation preferably comprises
(a) 0.01 to 5.0 wt.-%, preferably 0.1 to 5.0 wt.-%, more preferably 0.1 to 3.5 wt.-%, of the sulfonic acid (SA) and
(b) 0.01 to 20 wt.-%, preferably 0.05 to 10 wt.-%, more preferably 0.05 to 5.0 wt.-%, of the carboxylic acid(s) (CA) based on the total formulation.

If the formulation according to the invention is a concentrate (must be diluted prior to use), the formulation preferably comprises
(a) 0.1 to 80 wt.-%, preferably 0.5 to 50 wt.-%, more preferably 1.0 to 35 wt.-%, of the sulfonic acid (SA) and
(b) 0.1 to 80 wt.-%, preferably 1.0 to 60 wt.-%, more preferably 1.0 to 50 wt.-%, of the carboxylic acid(s) (CA) based on the total formulation.

One essential component of the formulation is the carboxylic acid (CA). According to the invention the carboxylic acid (CA) is selected from the group consisting of mono-carboxylic acid, di-carboxylic acid and tri-carboxylic acid. In a preferred embodiment the carboxylic acid (CA) is a mono-carboxylic acid or di-carboxylic acid, still more preferably the carboxylic acid (CA) is a mono-carboxylic acid.

The carboxylic acid (CA) according to this invention may comprise further functional groups like hydroxy groups (—OH) and/or double bonds (═). In one preferred embodiment the carboxylic acid (CA) comprises in addition to the carboxy group(s) (—CO$_2$H) one hydroxy group (—OH). In one specific embodiment the carboxylic acid (CA) comprises as functional group only the carboxy group(s) (—CO$_2$H), i.e. the carboxylic acid (CA) is an alkyl mono-carboxylic acid, alkyl di-carboxylic acid or alkyl tri-carboxylic acid, most preferably an alkyl mono-carboxylic acid. In one more specific embodiment the carboxylic acid (CA) is a linear C$_2$ to C$_{10}$ alkyl mono-carboxylic acid or branched C$_2$ to C$_{10}$ alkyl mono-carboxylic acid.

Accordingly the carboxylic acid (CA) is preferably selected from the group consisting of formic acid, acetic acid, propanoic acid, oxalic acid, lactic acid, citric acid, tartaric acid, mandelic acid, benzoic acid, salicylic acid, glutaric acid, sorbic acid and succinic acid.

In one specific embodiment the carboxylic acid (CA) does not contain an aromatic moiety. Accordingly the carboxylic acid (CA) is preferably selected from the group consisting of formic acid, acetic acid, propanoic acid, oxalic acid, lactic acid, citric acid, tartaric acid, glutaric acid, sorbic acid and succinic acid.

More preferably the carboxylic acid (CA) is a non-aromatic mono-carboxylic acid. Accordingly the carboxylic acid (CA) is preferably selected from the group consisting of formic acid, acetic acid, propanoic acid, lactic acid, and sorbic acid.

Still more preferably the carboxylic acid (CA) is an alkyl mono-carboxylic acid selected from the group consisting of formic acid, acetic acid, and propanoic acid.

In one preferred embodiment the carboxylic acid (CA) is formic acid.

The other essential component of the present invention is the sulfonic acid (SA) of formula (I)

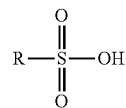

wherein
R is selected from the group consisting of linear alkyl residue, branched alkyl residue, linear alkenyl residue, and branched alkenyl residue; and Preferably the residue R being an alkyl has C$_1$ to C$_{20}$ carbon atoms whereas the residue R being an alkenyl has C$_2$ to C$_{20}$ carbon atoms.

Accordingly it is preferred that the linear alkyl residue is selected from the group consisting of methyl, ethyl, n-propyl, n-butyl, n-pentyl, n-hexyl, n-heptyl, n-octyl, n-nonyl, and n-decyl, more preferably the linear alkyl residue is selected from the group consisting of methyl, ethyl, n-propyl, n-butyl, n- and pentyl. In one specific embodiment the linear alkyl residue is methyl, ethyl or n-propyl, especially methyl.

In case the residue R is a branched alkyl residue it is preferred that R is iso-propyl or ter-butyl.

Accordingly in a preferred embodiment the residue R is preferably selected from the group consisting of methyl, ethyl, n-propyl, iso-propyl, n-butyl, ter-butyl, n-pentyl and n-hexyl, more preferably the residue R is methyl or ethyl. In one preferred embodiment the residue R is methyl.

Therefore, in one specific embodiment the formulation of the present invention comprises methane sulfonic acid (H$_3$C—SO$_3$H) and/or formic acid (HCO$_2$H).

Thus in one specific embodiment, if the formulation according to the invention is used undiluted ("ready-to-use"), the formulation comprises
(a) 0.01 to 5.0 wt.-%, preferably 0.1 to 5.0 wt.-%, more preferably 0.1 to 3.5 wt.-%, of methane sulfonic acid (H$_3$C—SO$_3$H) and
(b) 0.01 to 20 wt.-%, preferably 0.05 to 10 wt.-%, more preferably 0.05 to 5.0 wt.-%, of formic acid (HCO$_2$H) based on the total formulation.

In another specific embodiment, if the formulation according to the invention is a concentrate (must be diluted prior to use), the formulation comprises
(a) 0.1 to 80 wt.-%, preferably 0.5 to 50 wt.-%, more preferably 1.0 to 35 wt.-%, of of methane sulfonic acid (H$_3$C—SO$_3$H) and
(b) 0.1 to 80 wt.-%, preferably 1.0 to 60 wt.-%, more preferably 1.0 to 50 wt.-%, of formic acid (HCO$_2$H) based on the total formulation.

The formulation of the present invention may comprise further compounds, especially those which can further improve biocidal activity. Thus in one embodiment the formulation comprises additionally a chloro benzene derivative (CB), preferably a chloro benzene derivative (CB) of formula (II)

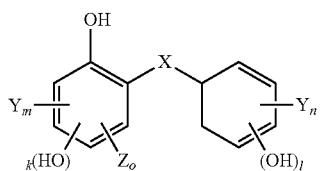

(II)

wherein
X is O, S or —CH$_2$—, preferably O or —CH$_2$—, more preferably O,
Y is Cl or Br, preferably Cl,
Z is SO$_2$H, NO$_2$ or C$_1$ to C$_4$ alkyl, preferably SO$_2$H,
k is 0 or 1, preferably 0,
l is 0 or 1, preferably 0,
m is 0, 1, 2, or 3, preferably 1,
n is 0, 1, 2, or 3, preferably 1 or 2,
o is 0 or 1, preferably 0.

Accordingly the chloro benzene derivative (CB) is preferably of formula (IIa)

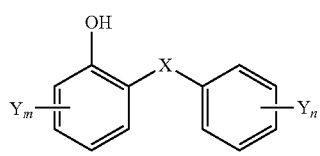

(IIa)

wherein
X is O or —CH$_2$—, preferably O,
Y is Cl or Br, preferably Cl,
m is 0, 1, 2, or 3, preferably 1,
n is 0, 1, 2, or 3, preferably 1 or 2.

Still more preferably the chloro benzene derivative (CB) is of formula (IIb)

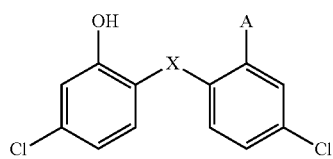

(IIb)

wherein
X is O or —CH$_2$—, preferably O,
A is H or Cl, preferably H.

In case the formulation of the present invention comprises in addition to the sulfonic acid (SA) and the carboxylic acid (CA) a chloro benzene derivative, and further said formulation is used undiluted ("ready-to-use"), said formulation preferably comprises
(a) 0.01 to 5.0 wt.-%, more preferably 0.1 to 5.0 wt.-%, still more preferably 0.1 to 3.5 wt.-%, of the sulfonic acid (SA), like the methane sulfonic acid (H$_3$C—SO$_3$H),
(b) 0.01 to 20.0 wt.-%, preferably 0.05 to 10.0 wt.-%, more preferably 0.05 to 5.0 wt.-%, of the carboxylic acid (CA), like the formic acid (HCO$_2$H), and
(c) 0.01 to 2.0 wt.-%, preferably 0.01 to 1.0 wt.-%, of the chloro benzene derivative (CB), like the chloro benzene derivative (CB) of formula (IIb) wherein X is O and A is H, based on the total formulation.

In another specific embodiment, in case the formulation of the present invention comprises in addition to the sulfonic acid (SA) and the carboxylic acid (CA) a chloro benzene derivative, and said formulation is used as a concentrate (must be diluted prior to use), said formulation comprises
(a) 0.1 to 80 wt.-%, preferably 0.5 to 50 wt.-%, more preferably 1.0 to 35 wt.-%, of of methane sulfonic acid (H$_3$C—SO$_3$H),
(b) 0.1 to 80 wt.-%, preferably 1.0 to 60 wt.-%, more preferably 1.0 to 50 wt.-%, of formic acid (HCO$_2$H), and
(c) 0.01 to 10.0 wt.-%, preferably 0.01 to 5.0 wt.-%, of the chloro benzene derivative (CB), like the chloro benzene derivative (CB) of formula (IIb) wherein X is O and A is H, based on the total formulation.

The above defined formulations show very good biocidal, especially antimicrobial, activity. Accordingly the present invention is also directed to the use of the formulation according to this invention as an antimicrobial, especially as a bactericide and/or fungicide. The terms like biocidal or antimicrobial are understood as commonly used in this technical field. Accordingly the term "biocide" preferably is used to describe all agents that kill microbial life and thus encompasses "antimicrobial agents". In turn the class of "antimicrobials" covers "antibacterials" ("bactericide") which are used against bacteria and "antifungals" ("fungicide") which are used against fungi.

In a more explicit definition the term bactericidal formulation is used for such formulations that pass the criteria according to the European standard methods EN 1040 (2006) and/or EN 1276 (2009). Likewise fungicidal formulations would be defined as formulations that pass the criteria according to the European standard methods norms EN 1275 (2006) and/or EN1650 (2008)

Preferably the formulation according to this invention can be effectively used against the bacteria selected from the group consisting of *Escherichia coli*, e.g. the strain ATCC 10536, *Enterococcus hirae*, e.g. the strain ATCC 10541, *Pseudomonas aeruginosa*, e.g. the strain ATCC 15442, *Staphylococcus aureus*, e.g. the strain ATCC 6538, *Klebsiella pneumonia*, e.g. the strain ATCC 4352, *Salmonella Typhimurium*, e.g. the strain ATCC 13311, *Lactobacillus brevis*, e.g. the strain DSM 6235, *Enterobacter cloacae*, e.g. the strain DSM 6234, *Klebsiella pneumoniae*, e.g. the strain ATCC 4352, and *Salmonella choleraesuis*, e.g. the strain ATCC 9184.

Preferably the formulation according to this invention can be also effectively used against the fungi selected from the group consisting of Canica albicans, e.g. the strain ATCC 10231, Aspergillius Niger, e.g. the strain ATCC 16404, *Saccharomyces cerevisiae*, e.g. the strain DSM 1333, and *Saccharomyces cerevisiae* var. diastaticus, e.g. the strain DSM 70487.

Formulations comprising additionally the chloro benzene derivative (CB) are also used for treatment of inanimate hard and soft surfaces in order to obtain a long-lasting bacteriostatic effect. Thus, the growth and reproduction of bacteria present on those treated inanimate surfaces is inhibited by the treatment for up to several weeks, like up to three weeks.

As the present formulation has very good antimicrobial, especially bactericidal and/or fungicidal, activity, the formulation of the present invention is especially used for antimicrobial treatment, like bactericidal and/or fungicidal treatment, antimicrobial accoutrement, like bactericidal and/or fungicidal accoutrement, desodoration, descaling, disinfection preferably of inanimate surfaces and materials, and/or sanitization preferably of inanimate surfaces and materials.

Therefore in one specific embodiment the present invention is directed to the use of the formulation as defined herein as
(a) a home care formulation, such as a disinfectant, all purpose cleaner, dishwashing liquid, descaling agent, a bath room cleaner, a toilet bowl cleaner,
and/or
(b) a disinfectant and/or sanitary detergent of hard and/or soft surfaces, such as a floor cleaner, a glass cleaner, a kitchen cleaner, a bath room cleaner, a sanitary cleaner, a toilet bowl cleaner, a furniture cleaner,
and/or
(c) a product for clean in place (CIP).

CIP applications are preferably used in the food and beverage industry, like in breweries, in the dairy industry, in the sof-drink and juice manufacturing industry, but also in the cosmetic and pharmaceutical industry.

The invention is also directed to the use of the formulation for the manufacture of
(a) a home care formulation, such as a disinfectant, all purpose cleaner, dishwashing liquid, descaling agent, a bath room cleaner, a toilet bowl cleaner,
and/or
(b) a disinfectant and/or sanitary detergent of hard and/or soft surfaces, such as a floor cleaner, a glass cleaner, a kitchen cleaner, a bath room cleaner, a sanitary cleaner, a toilet bowl cleaner, a furniture cleaner,
and/or
(c) a product for clean in place (CIP).

Finally, the invention is also directed to a product selected from the group consisting of home care formulation, a disinfectant of hard and/or soft surfaces, sanitary detergent of hard and/or soft surfaces, and product for clean in place (CIP), wherein said article comprises, preferably comprises at least 70 wt.-% of, still more preferably comprises at least 90 wt.-% of, yet more preferably consists of, the formulation as described herein. Accordingly the present invention is especially directed to a product selected from the group consisting of disinfectant, all purpose cleaner, dishwashing liquid, descaling agent, bath room cleaner, toilet bowl cleaner, floor cleaner, glass cleaner, kitchen cleaner, sanitary cleaner, furniture cleaner and product for clean in place (CIP), wherein said product comprises, preferably comprises at least 70 wt.-% of, still more preferably comprises at least 90 wt.-% of, yet more preferably consists of, the formulation as described herein.

Like the formulation also the products containing the formulation of the present invention can be used as concentrate that has to be diluted with water prior to use or are ready-to-use products, which are used as such, e.g. without dilution.

The terms used in the previous paragraphs are understood according to the knowledge of the skilled artisan in the respective technical field. For instance a disinfectant is a substance that is applied to non-living (i.e. inanimate) objects to destroy microorganisms that are living on said objects. On the other hand the clean in place is a method of cleaning and/or disinfecting the interior surfaces of pipes, vessels, process equipment, filters and associated fittings without disassembly. The clean in place product according to this invention is especially used for removing soils and disinfection in facilities for processing typically liquid product streams such as beverages, milk, juices, etc. The formulation of the invention can be used for disinfection of the interior surfaces in CIP after a separate cleaning step. The cleaning step is performed with a cleaning formulation that is not biocidal or disinfecting. It may however also be the case that the formulation of the invention is used for CIP-cleaning and CIP disinfection in one single step.

Depending on the end application the formulation may contain further ingredients making it ready for the desired end-use. Such ingredients are known to the skilled artisan and do not contribute to the present invention. Depending upon the form of the formulation used at the end it comprises, in addition to the components mentioned above further constituents, for example surfactants (surface active agents), pH regulators, buffering agents, hydrotropes, polymers, metal sequestering or metal chelating agents, colourings, perfume oils, thickening or solidifying agents (consistency regulators), emulsifiers, emollients, UV-absorbers, and antioxidants.

Surface active agents will normally comprise at least one surfactant which may be anionic, cationic, nonionic or amphoteric. They are for instance described in the disclosure IP.com Journal (2011), 12(1A), IPCOM000213522D, published on 20 Dec. 2011 in section (b). In many cases, however, it has been found advantageous to select the surfactants from anionic, and especially zwitterionic and/or non-ionic surfactants.

Examples of cationic surfactants that can be used in the preparations (compositions) according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethy-lammonium chloride, lauryldimethylammonium chloride, lauryldimethylbenzylammonium chloride and tricetylmethylammonium chloride. Further cationic surfactants that can be used in accordance with the invention are quaternised protein hydrolysates.

Also suitable in accordance with the invention are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially page 45, line 9 to page 55, line 2.

Alkylamidoamines, especially fatty acid amidoamines, such as the stearylamidopropyl-dimethylamine obtainable under the name Tego Amid® 18, are distinguished not only by a good conditioning action but also especially by their good biodegradability. Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquat®100, according to CTFA nomenclature a "lauryl methyl gluceth-10 hydroxypropyl dimonium chloride".

The anionic surfactants are characterised by an anionic group that imparts water solubility, for example a carboxylate, sulfate, sulfonate or phosphate group, and a lipophilic alkyl group having approximately from 10 to 22 carbon atoms. In addition, glycol or polyglycol ether groups, ester, ether and amide groups and also hydroxy groups may be present in the molecule. Such substances are generally in the form of their water-soluble salts, such as the alkali metal, ammonium or amine salts. Examples of such salts include lithium, sodium, potassium, ammonium, triethylamine, ethanolamine, diethanolamine and triethanolamine salts. The sodium, potassium or ammonium (NR1R2R3) salts, especially, are used, with R1, R2 and R3 each independently of the others being hydrogen, C1-C4alkyl or C1-C4hydroxyalkyl.

The following are examples of suitable anionic surfactants, each in the form of sodium, potassium or ammonium salts or mono-, di- or tri-alkanolammonium salts having 2 or 3 carbon atoms in the alkanol group:

linear fatty acids having from 10 to 22 carbon atoms (soaps),
ether carboxylic acids of formula R—O—($CH_2$—$CH_2$—O)$_x$—$CH_2$—COOH, in which R is a linear alkyl group having from 10 to 22 carbon atoms and x=0 or from 1 to 16,
acyl sarcosides having from 10 to 18 carbon atoms in the acyl group,
acyl taurides having from 10 to 18 carbon atoms in the acyl group,
acyl isothionates having from 10 to 18 carbon atoms in the acyl group,
sulfosuccinic mono- and di-alkyl esters having from 8 to 18 carbon atoms in the alkyl group and sulfosuccinic monoalkylpolyoxyethyl esters having from 8 to 18 carbon atoms in the alkyl group and from 1 to 6 oxyethyl groups,
linear alkane sulfonates having from 12 to 18 carbon atoms,
linear α-olefin sulfonates having from 12 to 18 carbon atoms,
α-sulfo fatty acid methyl esters of fatty acids having from 12 to 18 carbon atoms,
alkyl sulfates and alkyl polyglycol ether sulfates of formula R'—O(CH2-CH2-O)x'—SO3H, in which R' is a preferably linear alkyl group having from 10 to 18 carbon atoms and x'=0 or from 1 to 12,
mixtures of surface-active hydroxysulfonates according to DE-A-3 725 030, especially page 3, lines 40 to 55,
sulfated hydroxyalkylpolyethylene and/or hydroxyalkylenepropylene glycol ethers according to DE-A-3 723 354, especially page 4, lines 42 to 62,
sulfonates of unsaturated fatty acids having from 12 to 24 carbon atoms and from 1 to 6 double bonds according to DE-A-3 926 344, especially page 2, lines 36 to 54,
esters of tartaric acid and citric acid with alcohols which are addition products of approximately from 2 to 15 molecules of ethylene oxide and/or propylene oxide with fatty alcohols having from 8 to 22 carbon atoms, or
anionic surfactants, as described in WO 00/10518, especially page 45, line 11 to page 48, line 3.

Preferred anionic surfactants are alkyl sulfates, alkyl polyglycol ether sulfates and ether carboxylic acids having from 10 to 18 carbon atoms in the alkyl group and up to 12 glycol ether groups in the molecule, and also especially salts of saturated and especially unsaturated $C_8$-$C_{22}$carboxylic acids, such as oleic acid, stearic acid, isostearic acid and palmitic acid.

Thus, as surfactant, there may also be used the salts of saturated and unsaturated C8-C22 fatty acids either alone or in the form of a mixture with one another or in the form of a mixture with other detergents or surfactants, e.g. as mentioned above. Examples of such fatty acids include, for example, capric, lauric, myristic, palmitic, stearic, arachidic, behenic, caproleic, dodecenoic, tetradecenoic, octadecenoic, oleic, eicosenoic and erucic acid, and the commercial mixtures of such acids, such as, for example, coconut fatty acid. Such acids are present in the form of salts, there coming into consideration as cations alkali metal cations, such as sodium and potassium cations, metal atoms, such as zinc and aluminium atoms, and nitrogen-containing organic compounds of sufficient alkalinity, such as amines and ethoxylated amines. Such salts may also be prepared in situ.

Especially preferred anionic surfactants in the composition according to the invention are monoethanolamine lauryl sulfate or the alkali metal salts of fatty alcohol sulfates, especially sodium lauryl sulfate and the reaction product of from 2 to 4 mol of ethylene oxide and sodium lauryl ether sulfate.

Surface-active compounds that carry at least one quaternary ammonium group and at least one —$COO^{(-)}$ or —$SO_3^{(-)}$ group in the molecule are termed zwitterionic surfactants. Zwitterionic surfactants that are especially suitable are the so-called betaines, such as the N-alkyl-N,N-dimethylammonium glycinates, for example cocoalkyldimethylammonium glycinate,
N-acylaminopropyl-N,N-dimethylammonium glycinates, for example cocoacylaminopropyldimethylammonium glycinate, and 2-alkyl-3-carboxymethyl-3-hydroxyethylimidazolines having from 8 to 18 carbon atoms in the alkyl or acyl group and also
cocoacylaminoethylhydroxyethylcarboxymethyl glycinate. A preferred zwitterionic surfactant is the fatty acid amide derivative known by the CTFA name cocoamidopropyl betaine.

Ampholytic surfactants are to be understood as meaning surface-active compounds that, in addition to a $C_{18}$-$C_{18}$-alkyl or -acyl group, contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Non-ionic surfactants are described in WO 00/10519, especially page 45, line 11 to page 50, line 12.

Suitable zwitterionic and amphoteric surfactants include C8-C18betaines, C8 C18sulfobetaines, C8-C24alkylamido-C1-C4alkylenebetaines, imidazoline carboxylates, alkylamphocarboxy-carboxylic acids, alkylamphocarboxylic acids (e.g. lauroamphoglycinate) and N-alkyl-☐-aminopropionates or -iminodipropionates, with preference being given to C10 C20alkylamido-C1-C4akylenebetaines and especially to coconut fatty acid amide propylbetaine.

Non-ionic surfactants contain as the hydrophilic group, for example, a polyol group such as a sugar, a polyalkylene glycol ether group or a combination of polyol and polyglycol ether groups.

Such compounds are, for example:
addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group,
$C_{12}$-$C_{22}$ fatty acid mono- and di-esters of addition products of from 1 to 30 mol of ethylene oxide with glycerol, $C_8$-$C_{22}$ alkyl-mono- and -oligo-glycosides and ethoxylated analogues thereof, addition products of from 5 to 60 mol of ethylene oxide with castor oil and hydrogenated castor oil, addition products of ethylene oxide with sorbitan fatty acid esters, addition products of ethylene oxide with fatty acid alkanolamides.

A further group are sugar surfactants which are glycosides or polyglycosides, for example of the general formula III:

R—O—$G_p$ where R=alkyl or alkenyl (e.g. C6-C20),
G=aldose or ketose and
p=1, 2, 3, 4, 5, 6, 7, 8, 9 or 10, is used.

In a further variant, the sugar surfactants to be used according to the invention are alkyl and/or alkenyl polyglycosides of the formula III in which R is an alkyl and/or alkenyl radical having 4 to 22 carbon atoms, G is a sugar radical having 5 or 6 carbon atoms and p is numbers from 1 to 10. In a further embodiment, the alkyl and/or alkenyl polyglycosides are derived from aldoses or ketoses having 5 or 6 carbon atoms.

The component G in formula III is selected in one embodiment from the group of hexoses, preferably from the group comprising allose, altrose, glucose, mannose, gulose, idose, galactose, talose, psicose, fructose, sorbose, tagatose, particularly preferably glucose.

In a further embodiment, the component G in formula III is selected from the group of pentoses, preferably the group comprising ribulose, xylulose, ribose, arabinose, xylose, lyxose, particularly preferably xylose and/or arabinose.

In one variant of the invention, the preferred alkyl and/or alkenyl oligoglycosides are alkyl and/or alkenyl oligoglucosides.

The index number p in the general formula III gives the degree of oligomerization (DP), i.e. the distribution of mono- and oligoglycosides, and is a number between 1 and 10. Whereas p in a given compound must always be an integer and here in particular can assume the values p=1 to 6, the value p for a certain alkyl (oligo)glycoside is an analytically determined calculated parameter which in most cases is a fraction. In one embodiment of the invention, alkyl and/or alkenyl oligoglycosides with an average degree of polymerization p of from 1.1 to 3.0 are used.

The alkyl and/or alkenyl polyglycosides according to the invention can be obtained by the relevant methods of preparative organic chemistry. By way of representation of the extensive literature, reference may be made here to the review paper by Biermann et al. in Starch/Stärke 45, 281 (1993), and also J. Kahre et al. in SÖFW-Journal volume 8, 598 (1995).

As well as alkyl and/or alkenyl polyglycosides based on unbranched fatty alcohols, in one variant, alkyl and/or alkenyl polyglycosides with branched radicals R are used.

In one embodiment, the radical R in formula III is selected from the group of alcohols comprising fatty alcohols, primary alcohols, in particular so-called oxo alcohols, for example nonyl, undecyl or tridecyl alcohols, and primary alcohols, which comprise linear octyl, decyl, dodecyl, tetradecyl, hexadecyl or octadecyl groups, and mixtures thereof.

In one variant, alcohols with a carbon chain, which may also be branched, having C4 C18, preferably C12-C16, in particular C12-C14, are selected.

In one embodiment of the invention, the branched radicals are isoamyl, isohexyl and/or isoheptyl, preferably 2-ethylhexyl and/or 2-propylheptyl.

According to the invention, it is also possible to use mixtures of different compounds of the general formula III. Thus, all combinations of the various aldoses or ketoses with all possible alkyl- and/or alkenyl radicals can be used. Nonionic surfactants as typically used include, for example, derivatives of the adducts of propylene oxide/ethylene oxide having a molecular weight of from 1000 to 15 000, fatty alcohol ethoxylates (1-50 EO), alkylphenol polyglycol ethers (1-50 EO), polyglucosides, alkylated glycosides and/or polyglycosides, ethoxylated hydrocarbons, fatty acid glycol partial esters, for example diethylene glycol monostearate, fatty acid alkanolamides and dialkanolamides, fatty acid alkanolamide ethoxylates and fatty amine oxides.

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The surfactants that are addition products of ethylene and/or propylene oxide with fatty alcohols or derivatives of such addition products may either be products having a "normal" homologue distribution or products having a restricted homologue distribution. "Normal" homologue distribution is to be understood as meaning mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts. The use of products having restricted homologue distribution may be preferred.

Examples for metal sequestering or metal chelating agents are described in They are described in the disclosure IP.com Journal (2011), 12(1A), IPCOM000213522D, published on 20 Dec. 2011 in section (e).

An embodiment of preference is a formulation of the invention, which is essentially free of enzymes. Also preferred is a formulation of the invention, which is essentially free of iodine and/or iodide. Further preferred is a formulation of the invention, which is essentially free of oxidants such as peroxo compounds, elemental halogen and halogen oxides or hydroxides. Formulations of special technical preference are essentially free of enzymes, iodine, iodide and oxidants.

The term "essentially free of iodine and/or iodide" in this context means that the concentration of iodine and/or iodide is less than 0.1 parts per one million parts of the formulation (<0.1 ppm). The term "essentially free of oxidants" in this context means that the concentration oxidants is less than 100 parts per one million parts of the formulation (<100 ppm), especially less than 10 parts per one million parts of the formulation (<10 ppm). The term "essentially free enzymes" in this context means that the concentration enzymes (such as proteases or lipases) is less than 10 parts per one million parts of the formulation (<10 ppm), especially less than 1 part per one million parts of the formulation (<1 ppm).

SUMMARY OF EMBODIMENTS

The present invention thus includes:

1. The use of a combination of
(a) a sulfonic acid of formula (I)

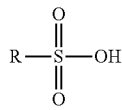

wherein
R is selected from the group consisting of linear alkyl residue, branched alkyl residue, linear alkenyl residue, and branched alkenyl residue; and
(b) at least one carboxylic acid selected from the group consisting of mono-carboxylic acid, di-carboxylic acid and tri-carboxylic acid, in the presence of
(d) at least one surfactant,
as an antimicrobial, especially as a bactericide and/or fungicide.

2. The use of a combination of
(a) a sulfonic acid of formula (I)

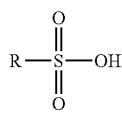

wherein
R is selected from the group consisting of linear alkyl residue, branched alkyl residue, linear alkenyl residue, and branched alkenyl residue; and
(b) at least one carboxylic acid selected from the group consisting of mono-carboxylic acid, di-carboxylic acid and tri-carboxylic acid, and
(c) a chloro benzene derivative,
as an antimicrobial, especially as a bactericide and/or fungicide.

3. The use of an aqueous formulation comprising, on 100 parts by weight (pbw) of the formulation,
(a) 0.5 to 5.0 pbw of a sulfonic acid of formula (I)

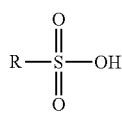

wherein
R is selected from the group consisting of linear alkyl residue, branched alkyl residue, linear alkenyl residue, and branched alkenyl residue; and
(b) 0.01 to 20.0 pbw of at least one carboxylic acid selected from the group consisting of mono-carboxylic acid, di-carboxylic acid and tri-carboxylic acid,
which formulation comprises at least 50 pbw of water,
as an antimicrobial, especially as a bactericide and/or fungicide.

4. The use of a formulation comprising
(a) a sulfonic acid of formula (I)

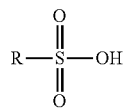

wherein
R is selected from the group consisting of linear alkyl residue, branched alkyl residue, linear alkenyl residue, and branched alkenyl residue; and
(b) at least one carboxylic acid selected from the group consisting of mono-carboxylic acid, di-carboxylic acid and tri-carboxylic acid, and
(c) a chloro benzene derivative,
as an antimicrobial, especially as a bactericide and/or fungicide.

5. The use of a formulation comprising
(a) a sulfonic acid of formula (I)

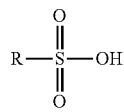

wherein
R is selected from the group consisting of linear alkyl residue, branched al-kyl residue, linear alkenyl residue, and branched alkenyl residue; and
(b) at least one carboxylic acid selected from the group consisting of mono-carboxylic acid, di-carboxylic acid and tri-carboxylic acid
as a home care formulation, such as an all purpose cleaner, dishwashing liquid, descaling agent, a bath room cleaner, a toilet bowl cleaner,
and/or as a disinfectant and/or sanitary detergent for hard surfaces, such as a floor cleaner, a glass cleaner, a kitchen cleaner, a bath room cleaner, a sanitary cleaner, a toilet bowl cleaner, a furniture cleaner.

6. The use of a combination or formulation of any of embodiments 1-5,
which formulation is essentially free of enzyme, iodine and iodide.

7. The use of a combination or formulation of any of embodiments 1-6,
which formulation is essentially free of elemental halogen, halogen oxides and halogen hydroxides.

8. The use of a combination or formulation of any of embodiments 1-7, wherein the residue R of formula (I) is selected from the group consisting of methyl, ethyl, n-propyl, iso-propyl, n-butyl, ter-butyl, n-pentyl and n-hexyl, preferably the residue R of formula (I) is methyl or ethyl.

9. The use of a combination or formulation of any of embodiments 1-8, wherein the carboxylic acid is selected from the group consisting of formic acid, acetic acid, propanoic acid, oxalic acid lactic acid, citric acid, tartaric, mandelic acid, benzoic acid, salicylic acid, glutar-ic acid, sorbic acid and succinic acid, preferably the carboxylic acid is selected from the group consisting of formic acid, acetic acid, and propanoic acid.

10. The use of a combination or formulation of any of embodiments 1-9, wherein
(a) the sulfonic acid of formula (I) is methane sulfonic acid, and
(b) the carboxylic acid is formic acid.

11. The use of a combination or formulation of any of embodiments 1-10 in the form of an aqueous formulation, preferably said aqueous formulation has a pH in the range of 0 to 4.0.

12. The use of a combination or formulation of any of embodiments 1-11, wherein the weight ratio of the sulfonic acid of formula (I) to the carboxylic acid is from the range 0.01 to 20.0.

13. The use of a formulation of any of embodiments 3-12, wherein said formulation is a ready-to-use formulation, said ready-to-use formulation comprises
(a) 0.1 to 5.0 wt.-% of the sulfonic acid of formula (I) and
(b) 0.05 to 40 wt.-%, preferably 0.05 to 5.0 wt.-%, of the carboxylic acid based on the total formulation.

14. The use of a combination or formulation of any of embodiments 1-13, wherein the combination or formulation comprises
(d) a surfactant selected from anionic, cationic, nonionic and amphoteric surfactants, preferably from anionic, nonionic and amphoteric surfactants, and especially from amphoteric surfactants and non-ionic surfactants.

15. The use of a formulation of any of embodiments 3-14, wherein the formulation comprises
(d) 0.1 to 40 wt.-% of a surfactant, and 50 to 99.8, especially 80 to 99.75 wt.-%, of water.

16. The use of a combination or formulation of any of embodiments 1-15 comprising
(c) a chloro benzene derivative, which is of the formula (II)

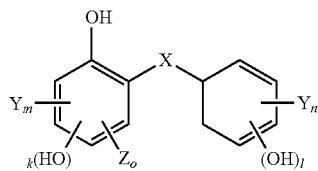

wherein
X is O, S or —CH$_2$—
Y is Cl or Br,
Z is SO$_2$H, NO2 or C1 to C4 alkyl,
k is 0 or 1,
l is 0 or 1,
m is 0, 1, 2, or 3,
n is 0, 1, 2, or 3,
o is 0 or 1,
and preferably is 4,4'-dichloro-2-hydroxydiphenylether.

17. A process for achieving an antimicrobial effect, especially an antibacterial and/or antifungal effect, on a hard surface, by contacting said surface with a liquid formulation of
(a) a sulfonic acid of formula (I)

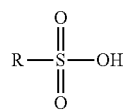

wherein
R is selected from the group consisting of linear alkyl residue, branched alkyl residue, linear alkenyl residue, and branched alkenyl residue; and (b) at least one carboxylic acid selected from the group consisting of mono-carboxylic acid, di-carboxylic acid and tri-carboxylic acid, in the presence of
(d) at least one surfactant.

18. A process for achieving an antimicrobial effect, especially an antibacterial and/or antifungal effect, on a hard surface, by contacting said surface with a liquid formulation of
(a) a sulfonic acid of formula (I)

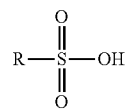

wherein
R is selected from the group consisting of linear alkyl residue, branched alkyl residue, linear alkenyl residue, and branched alkenyl residue; and
(b) at least one carboxylic acid selected from the group consisting of mono-carboxylic acid, di-carboxylic acid and tri-carboxylic acid, and
(c) a chloro benzene derivative.

19. A process for achieving an antimicrobial effect, especially an antibacterial and/or antifungal effect, on a hard surface, by contacting said surface with a liquid aqueous formulation comprising, on 100 parts by weight (pbw) of the formulation,
(a) 0.5 to 5.0 pbw of a sulfonic acid of formula (I)

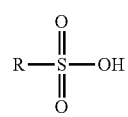

wherein
R is selected from the group consisting of linear alkyl residue, branched alkyl residue, linear alkenyl residue, and branched alkenyl residue; and
(b) 0.01 to 20.0 pbw of at least one carboxylic acid selected from the group consisting of mono-carboxylic acid, di-carboxylic acid and tri-carboxylic acid, and
(e) at least 50 pbw of water.

20. A formulation comprising
(a) a sulfonic acid of formula (I)

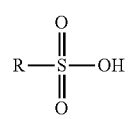

wherein
R is selected from the group consisting of linear alkyl residue, branched alkyl residue, linear alkenyl residue, and branched alkenyl residue;
(b) at least one carboxylic acid selected from the group consisting of mono-carboxylic acid, di-carboxylic acid and tri-carboxylic acid; and
(c) a chloro benzene derivative.

21. A formulation comprising
(a) a sulfonic acid of formula (I)

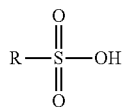

wherein
R is selected from the group consisting of linear alkyl residue, branched alkyl residue, linear alkenyl residue, and branched alkenyl residue;
(b) at least one carboxylic acid selected from the group consisting of mono-carboxylic acid, di-carboxylic acid and tri-carboxylic acid; and
(d) a surfactant;
provided that the formulation is essentially free of enzymes; and provided that the formulation is essentially free of oxidants and/or is essentially free of iodine and/or iodide.

22. Formulation according to embodiment 20 or 21, which contains
(c) a chloro benzene derivative of the formula (II)

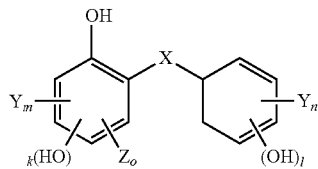

wherein
X is O, S or —CH2-
Y is Cl or Br,
Z is SO2H, NO2 or C1 to C4 alkyl,
k is 0 or 1,
l is 0 or 1,
m is 0, 1, 2, or 3,
n is 0, 1, 2, or 3,
o is 0 or 1,
which preferably is the compound 4,4'-dichloro-2-hydroxy-diphenylether.

23. Formulation according to any of the embodiments 20 to 22, which contains
(d) a surfactant selected from anionic, cationic, nonionic and amphoteric surfactants, preferably from anionic, nonionic and amphoteric surfactants, and especially from amphoteric surfactants and non-ionic surfactants.

24. Formulation according to any of the embodiments 20 to 23, wherein the residue R of formula (I) is selected from the group consisting of methyl, ethyl, n-propyl, iso-propyl, n-butyl, ter-butyl, n-pentyl and n-hexyl, preferably the residue R of formula (I) is methyl or ethyl.

25. Formulation according to any of the embodiments 20 to 24, wherein the carboxylic acid is selected from the group consisting of formic acid, acetic acid, propanoic acid, oxalic acid lactic acid, citric acid, tartaric, mandelic acid, benzoic acid, salicylic acid, glutaric acid, sorbic acid and succinic acid, preferably the carboxylic acid is selected from the group consisting of formic acid, acetic acid, and propanoic acid.

26. Formulation according to any of the embodiments 20 to 25, wherein the sulfonic acid of formula (I) is methane sulfonic acid and/or the carboxylic acid is formic acid.

27. Formulation according to any of the embodiments 20 to 26, wherein said formulation is an aqueous formulation, preferably said aqueous formulation has a pH in the range of 0 to 4.0.

28. Formulation according to any of the embodiments 20 to 27, wherein the weight ratio of the sulfonic acid of formula (I) to the carboxylic acid is in the range of 0.01 to 20.0.

29. Formulation according to any of the embodiments 20 to 28, which is an aqueous formulation containing
(e) at least 50 wt.-%, preferably 80 to 99.8 wt.-%, of water.

30. Formulation according to any of the embodiments 20 to 29, wherein said formulation is a ready-to-use formulation, said ready-to-use formulation comprises
(a) 0.1 to 5.0 wt.-% of the sulfonic acid of formula (I) and
(b) 0.05 to 40 wt.-%, preferably 0.05 to 5.0 wt.-%, of the carboxylic acid based on the total formulation.

31. Formulation according to any of the embodiments 20 to 30, wherein said formulation is a ready-to-use formulation, said ready-to-use formulation comprises
(a1) 0.01 to 5.0 wt.-% of the sulfonic acid of formula (I),
(a2) 0.01 to 20.0 wt.-% of the carboxylic acid, and
(a3) 0.01 to 2.0 wt.-% of the chloro benzene derivative.

32. Formulation according to embodiment 31, which contains
(a4) 0.1 to 40.0 wt.-% of the surfactant,
based on the total formulation.

33. Formulation according to embodiment 31 or 32, which is an aqueous formulation, especially comprising
(a5) 50 to 99.8, especially 80 to 99.75 wt.-%, of water.

34. Formulation according to any one of the embodiments 20 to 28, wherein said formulation is a concentrate, and said concentrate comprises
(a) 0.1 to 80 wt.-% of the sulfonic acid and
(b) 0.1 to 80 wt.-% of the carboxylic acid(s) based on the total formulation.

35. Formulation according to any one of the embodiments 20 to 28, wherein said formulation is a concentrated ready-to-use formulation comprising
(b1) 0.1 to 80 wt.-% of the sulfonic acid of formula (I),
(b2) 0.1 to 80 wt.-% of the carboxylic acid, and
(b3) 0.01 to 10.0 wt.-% of the chloro benzene derivative based on the total formulation.

36. Formulation according to embodiment 35, which contains
(b4) 1.0 to 89.8 wt.-% of the surfactant,
based on the total formulation.

37. Use of a formulation according to any one of the embodiments 20 to 36 as an antimicrobial, especially as a bactericide and/or fungicide.

38. Use of a formulation according to any one of the embodiments 20 to 36 for antimicrobial treatment, antimicrobial accoutrement, desodoration, descaling, dis-infection preferably of inanimate surfaces and materials and/or sanitization preferably of inanimate surfaces and materials.

39. Use of a formulation according to any of the embodiments 20 to 36 for the manufacture of
(a) a home care formulation, such as a disinfectant, all purpose cleaner, dish-washing liquid, descaling agent, a bath room cleaner, a toilet bowl cleaner,
and/or
(b) a disinfectant and/or sanitary detergent of hard and/or soft surfaces, such as a floor cleaner, a glass cleaner, a kitchen cleaner, a bath room cleaner, a sanitary cleaner, a toilet bowl cleaner, a furniture cleaner,
and/or
(c) a product for clean in place.

40. Use of a formulation according to any of the embodiments 20 to 36 as (a) a home care formulation, such as a disinfectant, all purpose cleaner, dish-washing liquid, descaling agent, a bath room cleaner, a toilet bowl cleaner, and/or (b) a disinfectant and/or sanitary detergent of hard and/or soft surfaces, such as a floor cleaner, a glass cleaner, a kitchen cleaner, a bath room cleaner, a sanitary cleaner, a toilet bowl cleaner, a furniture cleaner, and/or (c) a product for clean in place.

41. Product selected from the group consisting of home care formulation, disinfectant of hard and/or soft surfaces, sanitary detergent of hard and/or soft surfaces, product for clean in place, wherein said article comprises a formulation according to any one of the embodiments 20 to 36.

42. Product selected from the group consisting of disinfectant, all purpose cleaner, dishwashing liquid, descaling agent, bath room cleaner, toilet bowl cleaner, floor cleaner, glass cleaner, kitchen cleaner, sanitary cleaner, furniture cleaner and product for clean in place, wherein said article comprises a formulation according to any one of the embodiments 20 to 36.

In the following, the invention will be described in more detail by way of examples.

EXAMPLES

Examples 1 to 5

The following mixtures are prepared in water

| Example | MSA[1] [wt.-%] | formic acid [wt.-%] | E coli[2] log reduction | Ent hirae[3] log reduction | odour |
|---|---|---|---|---|---|
| 1 | 0 | 1.25 | >5 | <1 | Weak |
| 2 | 0 | 2.5 | >5 | 2.7 | medium |
| 3 | 1.25 | 0 | >5 | 2.8 | No |
| 4 | 1.25 | 0.625 | >5 | >5 | No |
| 5 | 2.5 | 0.625 | >5 | >5 | No |

[1]methane-sulfonic acid
[2]Escherichia coli
[3]Enterococcus hirae

The bactericidal efficacy on bacteria *Escherichia coli* ATCC 10536 and *Enterococcus hirae* ATCC 10541 of these mixtures is tested in a suspension test according to the European Standard EN1276:2009. Contact time is 5 Minutes, temperature is room temperature, e.g. 20 to 24° C., and dilution of the mixtures in the suspension test is 80%. There is added 0.3% bovine albumin solution to simulate dirty conditions. Neutralization is done with Caso-Bouillon+10 wt.-% Tween 80+3 wt.-% lecithin+0.3 wt.-% L-Histidine+ 0.5 wt.-% Sodium thiosulfate. The effectiveness of the neutralization procedure is checked according to the standard.

The log reductions are given in the table above.

The odour of the mixtures is assessed by sniffing.

It is found that not even the example 2 containing 2.5 wt.-% of formic acid alone (tested at 80% dilution) can kill both bacteria to a level of 5 log units as required by the standard. This mixture however has medium strong and clearly present (pungent) odour caused by the formic acid.

The example 4 containing 1.25 wt.-% methane sulfonic acid (MSA) and 0.625 wt.-% formic acid shows however a full bactericidal activity on both bacteria and does not show a pungent odour.

Examples 6 to 8

The following cleaner formulations are prepared.

| | | Example | | |
|---|---|---|---|---|
| | | 6[1] | 7[1] | 8[2] |
| Methane sulfonic acid | [wt.-%] | 0.95 | 2.00 | 2.50 |
| Formic acid | [wt.-%] | 0.50 | 0.50 | 1.00 |
| APG-type surfactant[3] | [wt.-%] | 6.30 | 6.30 | — |
| Thickening agent[4] | [wt.-%] | — | — | 3.00 |
| Anionic surfactant[5] | [wt.-%] | — | — | 1.00 |
| Sodium citrate[6] | | Up to pH = 2.0 | — | — |
| Water | [wt.-%] | Up to 100 | Up to 100 | Up to 100 |
| pH | [—] | 2.0 | 0.9 | 0.6 |
| Dilution factor | [%] | 80 | 80 | 25 |

[1]ready to use bath room cleaners
[2]toilet bowl cleaner
[3]Glucopon ® 215 UP ex BASF, trade product as is
[4]Arlypon ® VPC ex BASF, trade product as is
[5]Texapon ® EHS ex BASF, trade product as is
[6]tri-Sodium citrate-5,5-hydrate
[7]dilution factor in suspension test according to EN 1276:2009 (80% denotes 80% of the formulation plus 20% of water).

The bactericidal efficacy on bacteria *Escherichia coli* ATCC 10536 and *Enterococcus hirae* ATCC 10541 *Pseudomonas aeruginosa* ATCC 15442 and *Staphylococcus aureus* ATCC 6538 of these three formulations 6 to 8 is tested in a suspension test according to the European Standard EN1276:2009. Contact time is 5 Minutes, temperature is room temperature. Dilution of the formulations in the suspension test is as indicated in the table. There is added 0.3% bovine albumin solution to simulate dirty conditions. Neutralization is done with Caso-Bouillon+10 wt.-% Tween 80+3 wt.-% lecithin+0.3 wt.-% L-Histidine+0.5 wt.-% Sodium thiosulfate. The effectiveness of the neutralization procedure is checked according to the standard.

For all three formulations in the mentioned dilution a full activity (>5 log bacterial reduction) on all 4 bacteria is found.

None of the three formulations 6 to 8 had an unpleasant pungent odour

Examples 9 and 10

The following cleaner formulations are prepared.

| | | Example[1] | |
|---|---|---|---|
| | | 9 | 10 |
| Tinosan HP100[2] | [wt.-%] | 0.30 | 0.30 |
| Methane sulfonic acid | [wt.-%] | 0.95 | 2.00 |
| Formic acid | [wt.-%] | 0.50 | 0.50 |
| APG-type surfactant[3] | [wt.-%] | 6.30 | 6.30 |
| Sodium citrate[4] | | Up to pH = 2.0 | — |

-continued

| | | Example[1] | |
|---|---|---|---|
| | | 9 | 10 |
| water | [wt.-%] | Up to 100 | Up to 100 |
| pH | [—] | 2.0 | 0.9 |
| Dilution factor[5] | [%] | 80 | 80 |

[1]ready to use bath room cleaners
[2]Tinosan HP100 is a solution of 30 wt % 4,4'-dichloro-2-hydroxydiphenylether in 1-2 propylene glycol, supplied by BASF
[3]Glucopon ® 215 UP ex BASF, trade product as is
[4]tri-Sodium citrate-5,5-hydrate
[5]dilution factor in suspension test according to EN 1276

The bactericidal efficacy on bacteria *Escherichia coli* ATCC 10536 and *Enterococcus hirae* ATCC 10541 *Pseudomonas aeruginosa* ATCC 15442 and *Staphylococcus aureus* ATCC 6538 of these three formulations 9 and 10 is tested in a suspension test according to the European Standard EN1276:2009. Contact time is 5 Minutes, temperature is room temperature. Dilution of the formulations in the suspension test is as indicated in the table. There is added 0.3% bovine albumin solution to simulate dirty conditions. Neutralization is done with Caso-Bouillon+10 wt.-% Tween 80+3 wt.-% lecithin+0.3 wt.-% L-Histidine+0.5 wt.-% Sodium thiosulfate The effectiveness of the neutratlization procedure is checked according to the standard.

For both formulations 9 and 10 in the mentioned dilution a full activity (>5 log bacterial reduction) on all 4 bacteria is found.

None of the two formulations 9 and 10 has an unpleasant pungent odour.

Examples 11 to 15

The following mixtures are prepared in water

| Example | MAS[1] [wt.-%] | formic acid [wt.-%] | Can albicans[2] log reduction | odour [—] |
|---|---|---|---|---|
| 11 | 3.75 | 0 | <1 | No |
| 12 | 12.5 | 0 | <1 | No |
| 13 | 0 | 2.5 | 1.9 | medium |
| 14 | 0 | 3.75 | >4 | strong |
| 15 | 0.625 | 2.5 | >4 | medium |

[1]methane-sulfonic acid
[2]Candida albicans

The yeasticidal efficacy on Candida albicans ATCC 10231 of these mixtures is tested in a suspension test according to the European Standard EN1650:2008. Contact time is 15 Minutes, temperature is room temperature and dilution of the mixtures in the suspension test is 80%. There is added 0.3% bovine albumin solution to simulate dirty conditions. Neutralization is done with Caso-Bouillon+10 wt.-% Tween 80+3 wt.-% lecithin+0.3 wt.-% L-Histidine+0.5 wt.-% Sodium thiosulfate. The effectiveness of the neutratlization procedure is checked according to the standard.

The log reductions are given in the table above.

The odour of the mixtures is assessed by sniffing.

It is found that methanesulfonic acid (MAS) does not have any yeasticidal activity (example 12). The mixture containing 3.75 wt.-% of formic acid alone (mixture tested at 80% dilution) can kill *C. albicans* >4 Log within 15 minutes as required by the standard (example 14). This mixture however has a strong pungent odour caused by the formic acid.

The mixture containing 0.625 wt.-% methanesulfonic acid (MSA) and 2.5 wt.-% formic acid shows also a full yeasticidal activity and has only a medium strong pungent odour (example 15).

Examples 16 to 20

The cleaning performance of formulation according to examples 6 to 10 is tested according to the IKW drop test. In this test ceramic stripes (28×4 cm) are first soiled with a Ca-stearate dispersion The soil dispersion composition is: 5 wt.-% Ca-Stearate, 9.8 wt. % Water, 85 wt.-% Ethanol, 0.2 wt.-% Spezial Schwarz. The dosage is 6 ml per stripe. Then the stripes are heated to 180° C. for 1 hour. Subsequently, 25 μl of cleaning solution is put onto the slide, let penetrate for a defined time and then the stripe is rinsed with deionized water. Then the residue on the stripe is compared with the IKW table of comparison for assessment. The results are summarized in the table below. All examples show an excellent cleaning performance in this test without mechanical action.

| Example | Formulation of example | Time (s) until 100% cleaning performance |
|---|---|---|
| 16 | 6 | 300 |
| 17 | 7 | 300 |
| 18 | 8 | 300 |
| 19 | 9 | 450 |
| 20 | 10 | 300 |

Examples 21 and 22

The formulations of example 7 and 10 are also tested for their yeasticidal activity according to the details given for examples 11 to 15. Contact time is 15 minutes, temperature is room temperature, the formulations are tested in 80%.

Example 21

The acid formulation of example 7 without Tinosan HP100 shows a log reduction of only 1.2 after 15 minutes contact time.

Example 22

The same formulation, but, in addition with 0.3 wt.-% Tinosan HP100 (formulation of example 10) shows full activity with a log reduction of >4.

Examples 23 and 24

Test solutions containing formulations of example 6, 7, 9 and 10 are prepared as used for the suspension test described above. For the purpose of comparison, a market product comprising non-ionic tensides and 1.5% of formic acid (pH=0.9) is s diluted to obtain a comparative test solution. For testing corrosivity against plastics, a plastic test strip (HANSGROHE® spline/corrosion test) is dipped repeatedly into the test solution. The test strip is made from clear Plexiglass® 8N80 [PMMA] and contains a stainless steel pin tightly in a hole, providing a constant tension; the transparency of the test strip allows easy visual detection of fissures or cracks formed around the pin. The test strip is checked visually after 4 hours, 3 days, 7 days and 14 days.

The same test is performed using test strips made from clear Makrolon® 3103 [polycarbonate] and test strips made from clear Polylac® PA 727 [acrylnitrile-butadiene-styrene].

Result: None of the test strips used in contact with the cleaner of present example 6, 7, 9 or 10 shows any sign of fissures or cracks after 14 days, which indicates low corrosiveness and good compatibility of the present formulation with the plastics material. The test strips of clear Polylac® PA 727 [acrylnitrile-butadiene-styrene] used in contact with the comparative test solution show no sign of fissures or cracks after 14 days.

The test strips of clear Plexiglass® 8N80 [PMMA] used in contact with the comparative test solution show no sign of fissures or cracks after 4 hours, show fissures after 3 days, and show cracks after 7 days.

The test strips of clear Makrolon® 3103 [polycarbonate] used in contact with the comparative test solution show no sign of fissures or cracks after 3 days, and show fissures after 7 days.

The invention claimed is:

1. A process of using a combination of
(a) 0.1 to 5.0 wt. % based on the total combination of a sulfonic acid of formula (I)

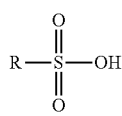

wherein R is selected from the group consisting of methyl and ethyl; and
(b) 0.05 to 20 wt. % based on the total combination of at least one carboxylic acid selected from the group consisting of formic acid, acetic acid, propanoic acid, oxalic acid lactic acid, citric acid, tartaric, mandelic acid, benzoic acid, salicylic acid, glutaric acid, sorbic acid, and succinic acid, in the presence of
(c) at least one surfactant, as an antimicrobial,
the process comprising:
contacting the combination with a surface or material.

2. A process of using an aqueous formulation comprising, on 100 parts by weight (pbw) of the formulation,
(a) 0.5 to 5.0 pbw of a sulfonic acid of formula (I)

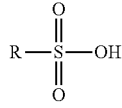

wherein R is selected from the group consisting of methyl and ethyl; and
(b) 0.05 to 20.0 pbw of at least one carboxylic acid selected from the group consisting of formic acid, acetic acid, propanoic acid, oxalic acid lactic acid, citric acid, tartaric, mandelic acid, benzoic acid, salicylic acid, glutaric acid, sorbic acid, and succinic acid,
which formulation comprises at least 50 pbw of water, as an antimicrobial,
the process comprising:
contacting the formulation with a surface or material.

3. A process of using a formulation comprising
(a) 0.1 to 5.0 wt. % based on the total formulation of a sulfonic acid of formula (I)

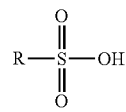

wherein R is selected from the group consisting of methyl and ethyl; and
(b) 0.05 to 20 wt. % based on the total formulation of at least one carboxylic acid selected from the group consisting of formic acid, acetic acid, propanoic acid, oxalic acid lactic acid, citric acid, tartaric, mandelic acid, benzoic acid, salicylic acid, glutaric acid, sorbic acid, and succinic acid, and
(c) a chloro benzene derivative,
as an antimicrobial, the process comprising:
contacting the formulation with a surface or material.

4. The process according to claim 2 wherein the formulation is
a home care formulation, such as selected from the group consisting of an all purpose cleaner, dishwashing liquid, descaling agent, a bathroom cleaner, and a toilet bowl cleaner, or
a disinfectant or sanitary detergent for hard surfaces, selected from the group consisting of a floor cleaner, a glass cleaner, a kitchen cleaner, a bathroom cleaner, a sanitary cleaner, a toilet bowl cleaner, and a furniture cleaner.

5. The process according to claim 2, wherein the formulation is essentially free of enzyme, iodine and iodide,
and is essentially free of elemental halogen, halogen oxides and halogen hydroxides.

6. The process according to claim 2, wherein the weight ratio of the sulfonic acid of formula (I) to the carboxylic acid is from the range 0.01 to 20.0;
and wherein the formulation has a pH within the range from 0 to 4.0.

7. The process according to claim 2, wherein the formulation further comprises
(c) a chloro benzene derivative, which is of the formula (II)

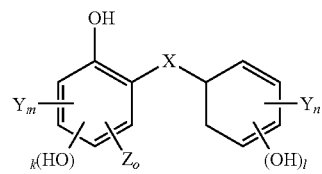

wherein
X is O, S or —CH2-
Y is Cl or Br,
Z is SO2H, NO2 or C1 to C4 alkyl,
k is 0 or 1,
l is 0 or 1,
m is 0, 1, 2, or 3,
n is 0, 1, 2, or 3,
o is 0 or 1,
at least one of n and m is greater than zero, and
at least one Y group is Cl,
where the chloro benzene derivative (c) is comprised in an amount from 0.01 to 10.0 wt.-%, and/or
(d) a surfactant selected from anionic, cationic, nonionic and amphoteric surfactants, where the surfactant (d) is comprised in an amount from 0.1 to 40 wt.-% besides 50 to 99.8 wt.-% of water,
where all percentages are relative to the total weight of the formulation.

8. A process for achieving an antimicrobial effect, on a hard surface, the process comprising:
contacting said hard surface with a liquid formulation of
(a) 0.1 to 5.0 wt. % based on the total formulation of a sulfonic acid of formula (I)

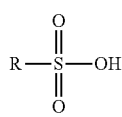

wherein R is selected from the group consisting of methyl and ethyl; and
(b) 0.05 to 20 wt. % based on the total formulation of at least one carboxylic acid selected from the group consisting of formic acid, acetic acid, propanoic acid, oxalic acid lactic acid, citric acid, tartaric, mandelic acid, benzoic acid, salicylic acid, glutaric acid, sorbic acid, and succinic acid,
in the presence of
(c) a chloro benzene derivative
and/or
(d) at least one surfactant.

9. A formulation comprising
(a) 0.1 to 5.0 wt. % based on the total formulation of a sulfonic acid of formula (I)

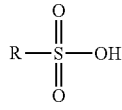

wherein R is selected from the group consisting of methyl and ethyl;
(b) 0.05 to 20 wt. % based on the total formulation of at least one carboxylic acid selected from the group consisting of formic acid, acetic acid, propanoic acid, oxalic acid lactic acid, citric acid, tartaric, mandelic acid, benzoic acid, salicylic acid, glutaric acid, sorbic acid, and succinic acid; and
(c) a chloro benzene derivative.

10. A formulation comprising
(a) 0.1 to 5.0 wt. % based on the total formulation of a sulfonic acid of formula (I)

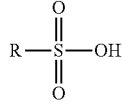

wherein R is selected from the group consisting of methyl and ethyl;
(b) 0.05 to 20 wt. % based on the total formulation of at least one carboxylic acid selected from the group consisting of formic acid, acetic acid, propanoic acid, oxalic acid lactic acid, citric acid, tartaric, mandelic acid, benzoic acid, salicylic acid, glutaric acid, sorbic acid, and succinic acid;
(c) a surfactant;
provided that the formulation is essentially free of enzymes; and provided that the formulation is essentially free of oxidants and is essentially free of iodine and iodide.

11. The formulation according to claim 10, further comprising
(d) a chloro benzene derivative of the formula (II)

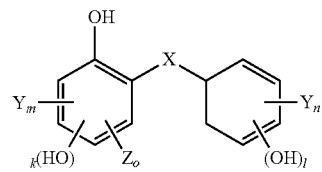

wherein
X is O, S or —CH2-
Y is Cl or Br,
Z is SO2H, NO2 or C1 to C4 alkyl,
k is 0 or 1,
l is 0 or 1,
m is 0, 1, 2, or 3,
n is 0, 1, 2, or 3,
o is 0 or 1,
at least one of n and m is greater than zero, and
at least one Y group is Cl,
and
wherein the surfactant is selected from anionic, cationic, nonionic and amphoteric surfactants.

12. The formulation according to claim 10, wherein said formulation is an aqueous formulation having, a pH in the range of 0 to 4.0 contains further comprises at least 50 wt.-%, of water.

13. The formulation according to claim 10, wherein the weight ratio of the sulfonic acid of formula (I) to the carboxylic acid is in the range of 0.01 to 20.0.

14. The formulation according to claim 9, wherein said formulation is a ready-to-use formulation, which comprises
(a1) 0.01 to 2.0 wt.-% of the chloro benzene derivative, and optionally further comprises
(a2) 0.1 to 40.0 wt.-% of the surfactant,
based on the total weight of the formulation;
or wherein said formulation is a concentrate, and said concentrate comprises
(b1) 0.01 to 10.0 wt.-% of the chloro benzene derivative, and optionally further comprises
(b2) 1.0 to 89.8 wt.-% of the surfactant,
based on the total formulation.

15. A process of using the formulation according to claim 10 as
(a) a home care formulation, selected from the group consisting of a disinfectant, all purpose cleaner, dishwashing liquid, descaling agent, a bathroom cleaner, and a toilet bowl cleaner, or
(b) a disinfectant or sanitary detergent of hard or soft surfaces, selected from the group consisting of a floor cleaner, a glass cleaner, a kitchen cleaner, a bathroom cleaner, a sanitary cleaner, a toilet bowl cleaner, and a furniture cleaner, or
(c) a product for clean in place, the process comprising:
contacting the formulation with a home care surface or material, a hard or soft surface, or a clean in place surface or material.

16. A product selected from the group consisting of home care formulation, disinfectant of hard or soft surfaces, sanitary detergent of hard or soft surfaces, product for clean in place, all purpose cleaner, dishwashing liquid, descaling agent, bathroom cleaner, toilet bowl cleaner, floor cleaner, glass cleaner, kitchen cleaner, sanitary cleaner, and furniture cleaner,
wherein said product comprises a formulation according to claim 10.

* * * * *